United States Patent
Kolb et al.

(10) Patent No.: US 6,797,856 B1
(45) Date of Patent: Sep. 28, 2004

(54) MICROBIAL MANAGEMENT IN SWIMWEAR

(75) Inventors: Thomas Mathias Kolb, Appleton, WI (US); Michael John Niemeyer, Appleton, WI (US); David W. Koenig, Menasha, WI (US); David Roland Otts, Appleton, WI (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 184 days.

(21) Appl. No.: 09/697,882

(22) Filed: Oct. 27, 2000

(51) Int. Cl.⁷ .............................. A61F 13/15
(52) U.S. Cl. ............... 604/360; 604/385.03; 604/367; 2/67; 424/76.1; 424/76.5
(58) Field of Search ................. 604/360, 367, 604/375, 382, 359, 366; 442/123, 118, 374, 121, 164; 2/67, 69.5–70; 424/76.1–76.5, 76.8, 46.2, 401, 65–69; 510/101, 293, 319, 383, 386, 405, 406, 462, 470; 210/764

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,922,723 A | 12/1975 | Popper |
| 4,059,114 A * | 11/1977 | Richards ............... 604/359 |
| 4,340,563 A | 7/1982 | Appel et al. |
| 4,615,880 A * | 10/1986 | Loth ................... 424/15 |
| 4,615,937 A * | 10/1986 | Bouchette ............ 442/123 |
| 4,617,326 A | 10/1986 | Björnberg et al. |
| 4,657,808 A | 4/1987 | Maggs |
| 4,692,374 A * | 9/1987 | Bouchette ............ 442/327 |
| 4,737,405 A * | 4/1988 | Bouchette ............ 442/327 |
| 4,837,079 A * | 6/1989 | Quantrille et al. ..... 442/123 |
| 4,911,899 A | 3/1990 | Hagiwara et al. |
| 4,983,392 A * | 1/1991 | Robinson ............. 424/427 |
| 4,985,023 A | 1/1991 | Blank et al. |
| 5,321,110 A * | 6/1994 | Shih .................. 526/264 |
| 5,416,929 A | 5/1995 | Braunstein |
| 5,509,913 A | 4/1996 | Yeo |
| 5,593,398 A | 1/1997 | Weimer |
| D377,980 S * | 2/1997 | Slingland ............ D24/126 |
| 5,631,074 A * | 5/1997 | Herlihy, Jr. .......... 442/35 |
| 5,792,132 A | 8/1998 | Garcia |
| 6,041,446 A | 3/2000 | Braunstein et al. |
| 6,195,800 B1 * | 3/2001 | Gilmer et al. ......... 2/67 |
| 6,228,491 B1 * | 5/2001 | Antelman ............. 428/372 |
| 6,433,244 B1 * | 8/2002 | Roe et al. ............ 604/391 |
| 2002/0023283 A1 * | 2/2002 | Kania et al. .......... 2/2.15 |

FOREIGN PATENT DOCUMENTS

| | | |
|---|---|---|
| JP | WO98/16400 | 4/1998 |
| WO | WO 98/44883 | 10/1998 |

* cited by examiner

Primary Examiner—Glenn K. Dawson
Assistant Examiner—Jacqueline F Stephens
(74) Attorney, Agent, or Firm—Pauley Petersen & Erickson

(57) ABSTRACT

An absorbent swimwear garment having a biocidal agent and/or a filtration agent attached to the garment for the purpose of killing or immobilizing microorganisms. During initial product use, the absorbent swim-wear garment is able to contain urine and bowel movements, just like ordinary diapers and training pants. When the swimwear garment is submersed in swim water, such as pool or lake water, the biocidal agent and/or filtration agent act to kill or immobilize any microorganisms deposited in the swim water from the urine and bowel movements contained in the garment. In one embodiment, a waist dam is formed in the garment around a wearer's waist, thereby providing a filtration barrier between the entrance and departure of swim water into and out of the garment.

26 Claims, 4 Drawing Sheets

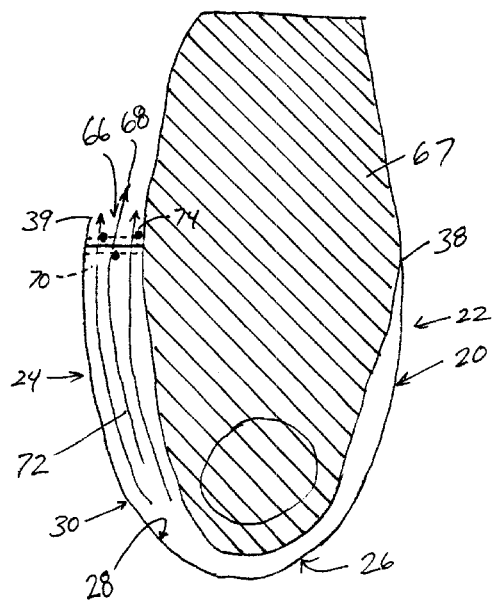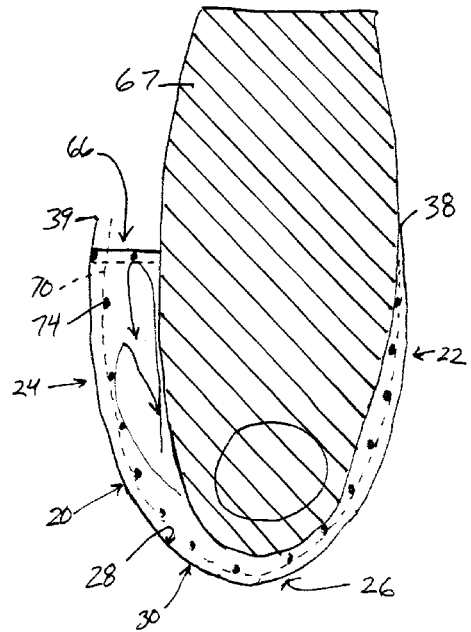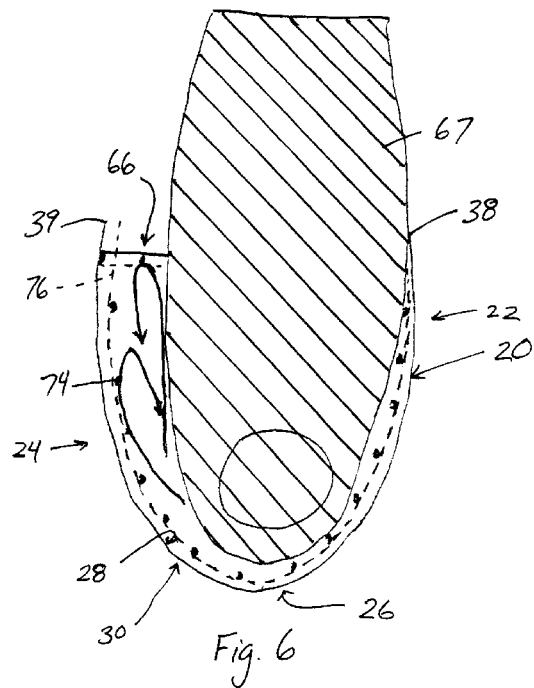

MICROBIAL MANAGEMENT IN SWIMWEAR

FIELD OF THE INVENTION

This invention is directed to swimpants and swimsuits for pre-toilet trained children. More particularly, the swimwear includes a biocidal or filtration agent for the purpose of killing or immobilizing microorganisms.

BACKGROUND OF THE INVENTION

Swim pants and swimsuits for pre-toilet trained children are designed to contain urine and bowel movements prior to swimming, just like ordinary diapers and training pants. Even though the absorbent swimwear is designed to prevent leakage of urine and bowel movements out of the garment and leakage of swim water into the garment, swim water inevitably tends to make its way into the garment. The swim water inside the garment mixes with the urine and bowel movements inside the garment and may re-enter the swimming environment along with microorganisms originating in the urine and bowel movements.

There is a need or desire for an absorbent swimwear garment that prevents the escape of active microorganisms into the swim water.

SUMMARY OF THE INVENTION

The present invention is directed to a pant-like absorbent swimwear garment, such as a swim pant or a swimsuit, that includes a biocidal or filtration agent to kill or immobilize microorganisms, thereby preventing the escape of active microorganisms into the swim water. More particularly, a filtration agent, or binding agent, can be attached to an outer cover, an absorbent assembly, or a body side liner, or another component of the garment such as a waist dam, a containment flap, or the like. The binding agent is capable of immobilizing microorganisms such as E. coli and other fecal associated bacteria, fungi and protozoans. A biocidal agent, or antimicrobial agent, can also be attached to the outer cover, the absorbent assembly, or the body side liner of the garment.

In one embodiment of the invention, a waist dam is constructed from a porous nonwoven web which contains a binding agent. The waist dam acts as a filter, filtering swim water as it leaves the garment through the waist dam. In another embodiment of the invention, a waist dam is constructed from a non-porous material with the binding agent fixed on the inner surfaces of the garment. In this embodiment, water exchange between the inside and outside of the garment is limited, thus providing sufficient time to immobilize the microorganisms. Alternatively, an antimicrobial agent can be attached to the waist dam.

In yet another embodiment of the invention, the garment includes a pair of containment flaps around the leg openings of the garment. The containment flaps provide additional protection against leakage. A binding agent and/or an antimicrobial agent can be attached to the containment flaps.

The resulting product is an absorbent swimwear garment that provides microbial management in the form of binding agents and/or antimicrobial agents attached to any one or more components of the swimwear garment. These binding agents and antimicrobial agents immobilize or kill microorganisms originating in the waste products deposited by the wearer in the absorbent garment, thereby resulting in reduced contamination of the swim water.

With the foregoing in mind, it is a feature and advantage of the invention to provide an absorbent swimwear garment with a microbial management system.

DEFINITIONS

Figure 1:
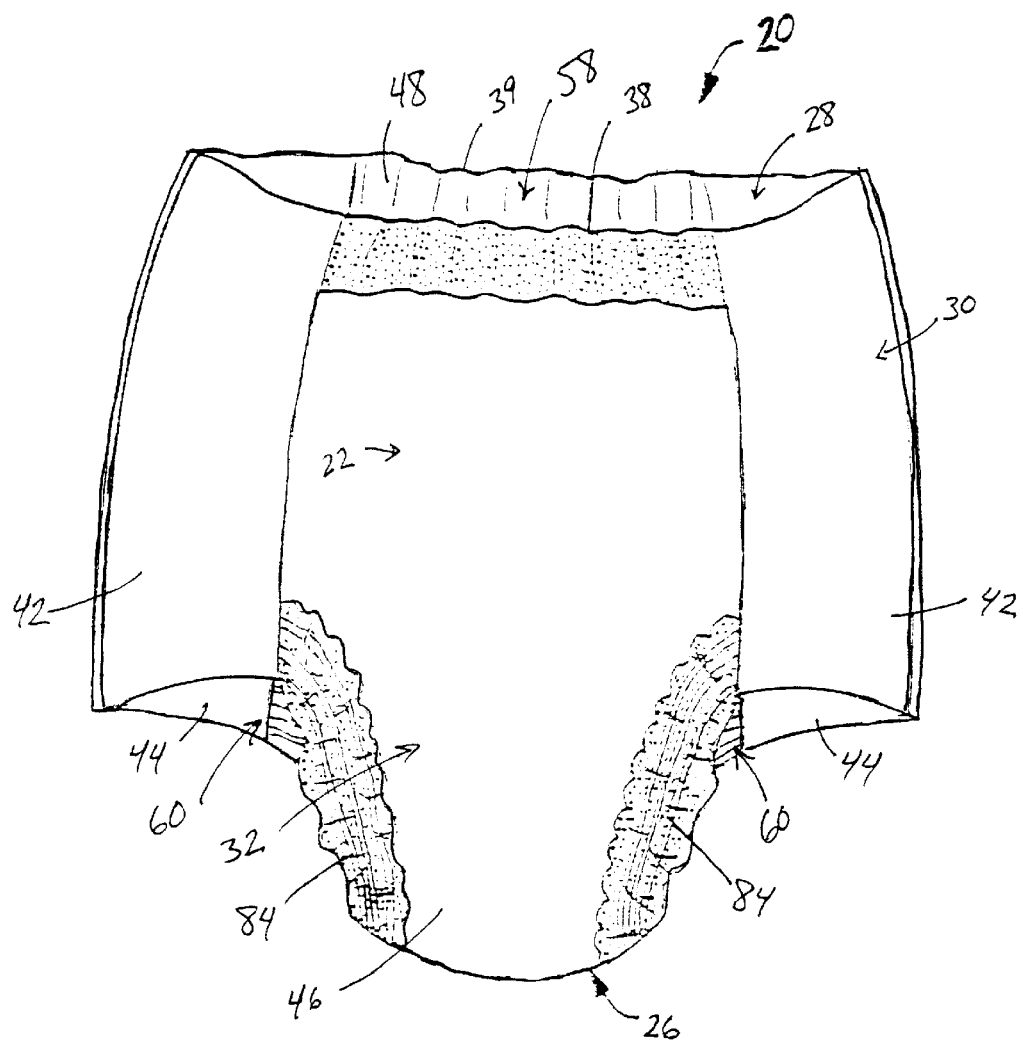
FIG. 1 is a front perspective view of an absorbent swimpant.

Within the context of this specification, each term or phrase below will include the following meaning or meanings.

"Elastic," "elasticized" and "elasticity" mean that property of a material or composite by virtue of which it tends to recover its original size and shape after removal of a force causing a deformation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid-impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid-impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material, but may be small enough to permit the flow of liquid water only above a minimum hydrostatic pressure.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process. "Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to an absorbent swimwear garment having a microbial management system for killing or immobilizing microorganisms in swim water, such as pool or lake water, inside the garment during swimming. The principles of the present invention can be incorporated into disposable, pant-like, absorbent swimwear articles, such as swimpants and swimsuits.

Figure 2:
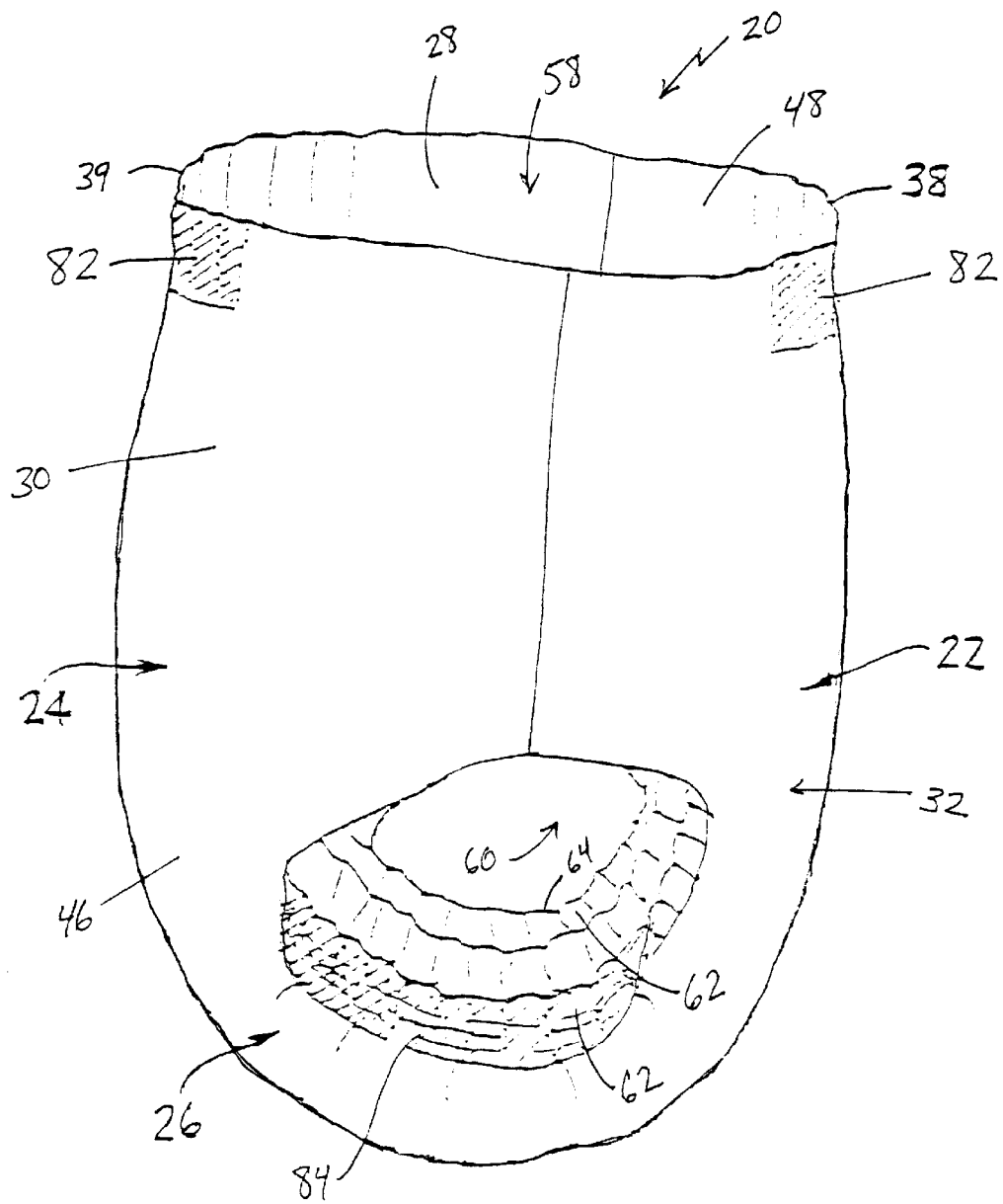
FIG. 2 is a side perspective view of an absorbent swimpant.

Referring to FIGS. 1 and 2, an absorbent swimpant 20 is illustrated. The swimpant 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing.

Figure 3:
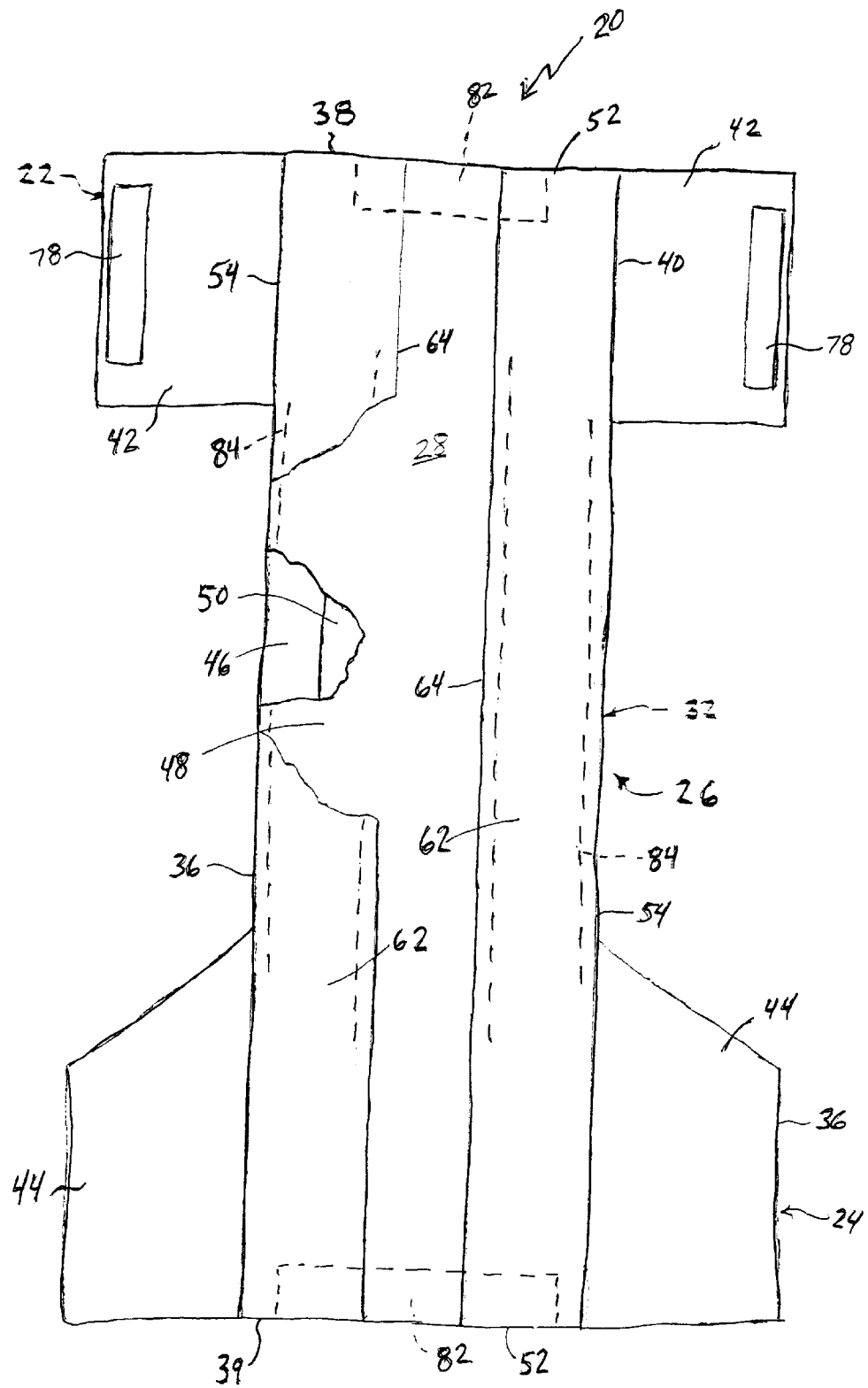
FIG. 3 is a plan view of an absorbent swimpant in a partially disassembled, stretched flat state, and showing the surface of the swimpant that faces the wearer when the swimpant is worn, and with portions cut away to show the underlying features.
Figure 1:
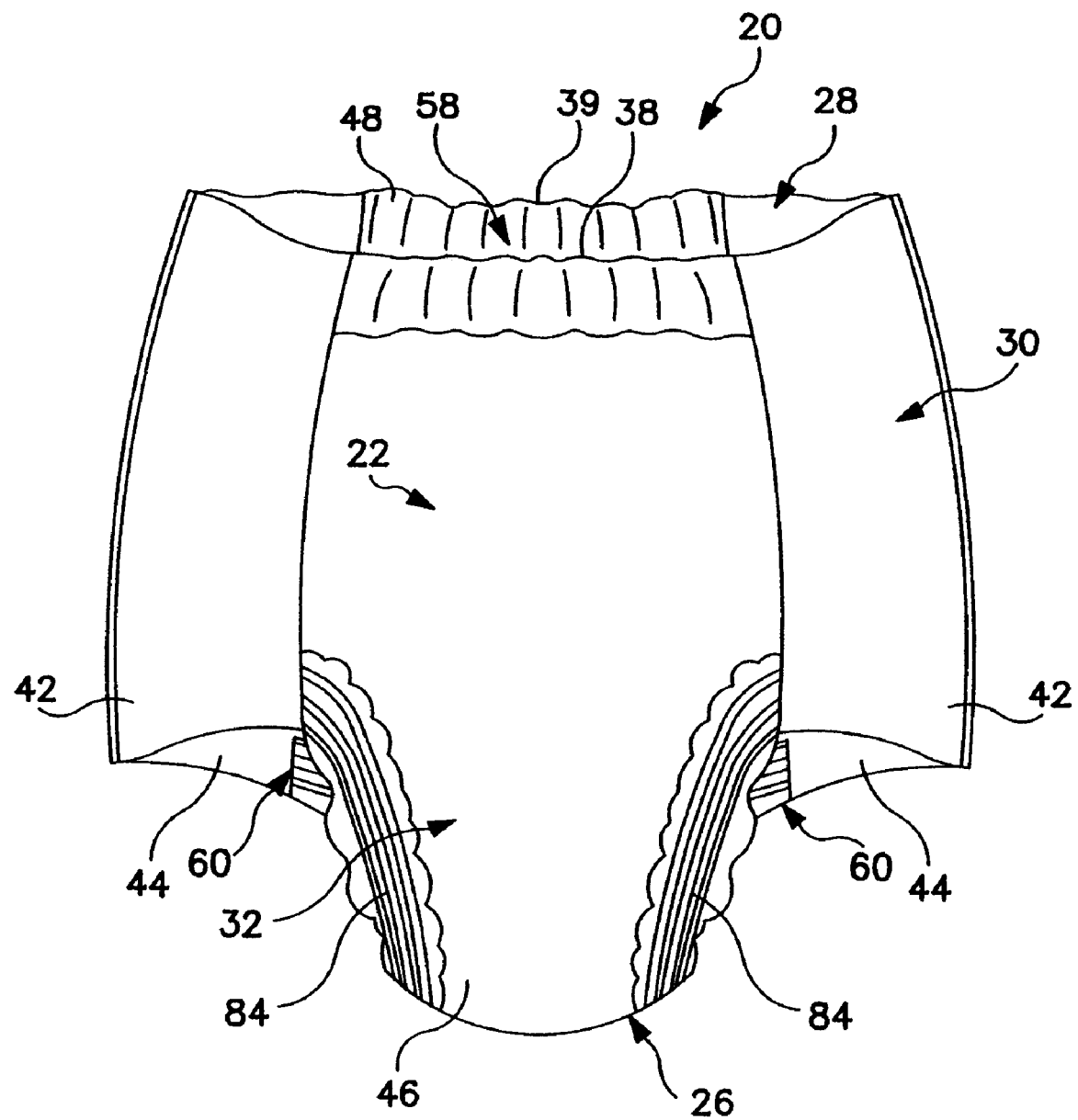
Figure 2:
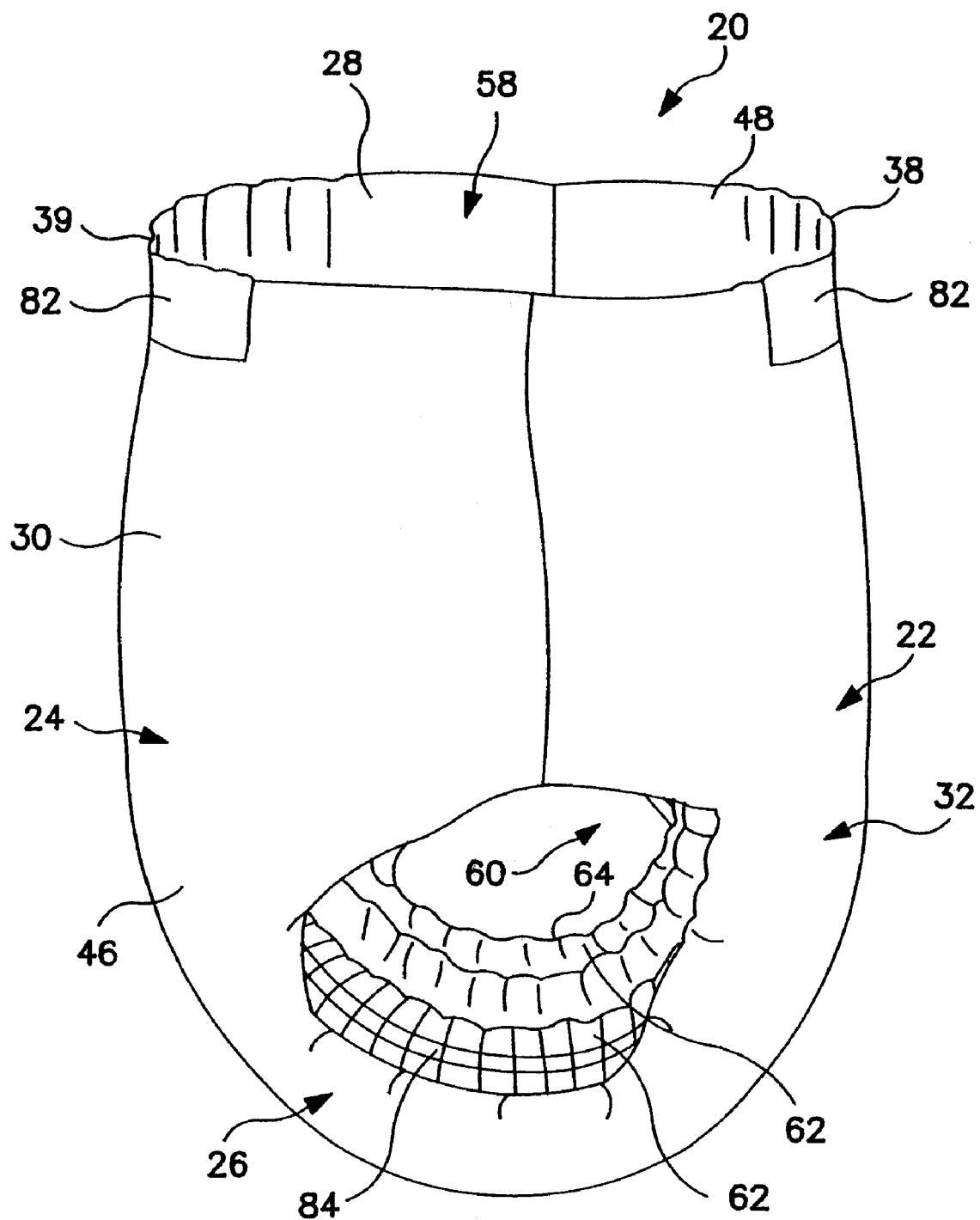
Figure 3:
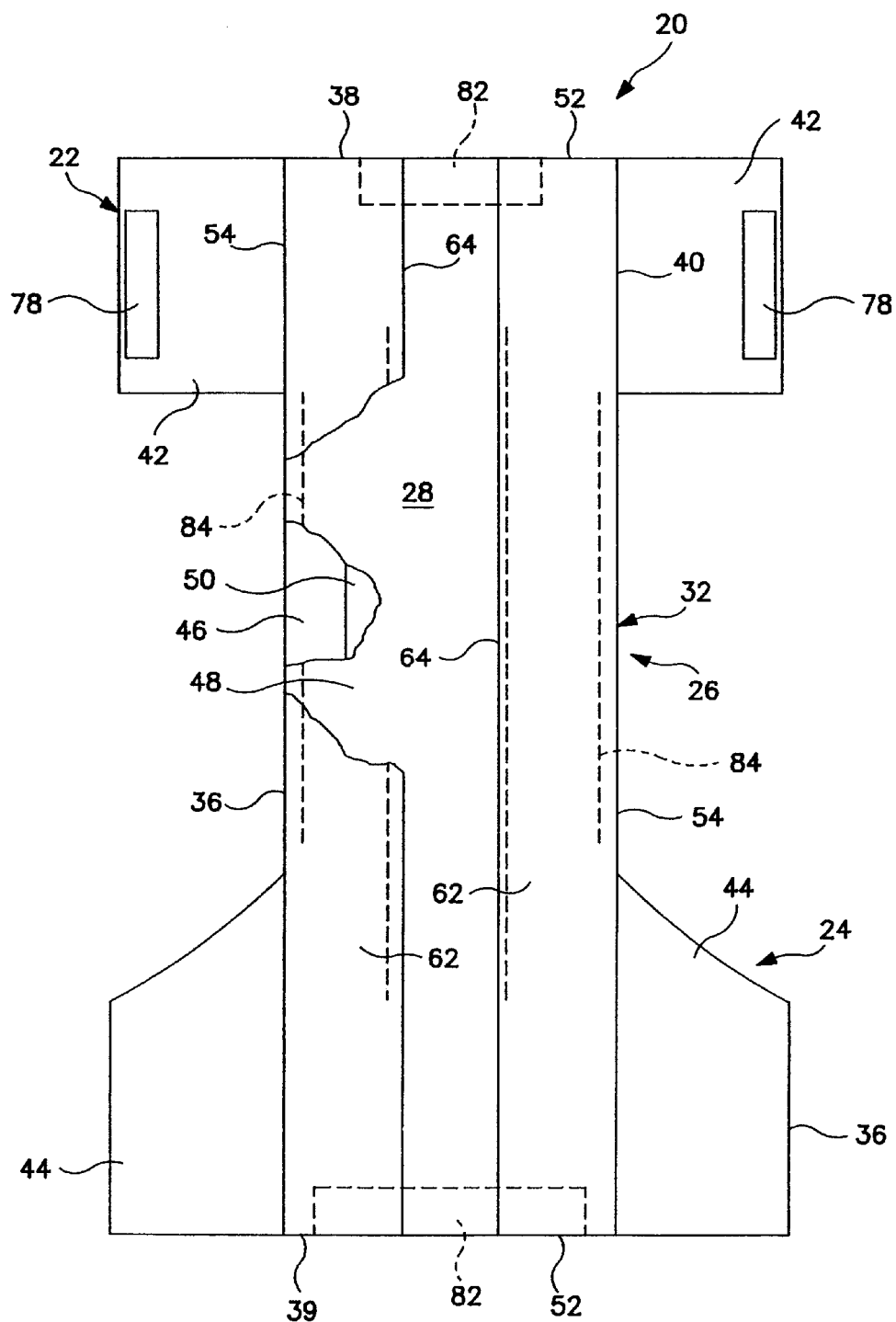

Referring to FIG. 3, the swimpant 20 is shown in a partially disassembled, stretched flat state, showing the inner surface 28 which faces the wearer when the garment is worn. As shown, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a somewhat rectangular composite structure 40, a pair of transversely opposed front side panels 42, and a pair of transversely opposed back side panels 44. The composite structure 40 and side panels 42 and 44 may be integrally formed, as shown in FIG. 2, or may include two or more separate elements, as shown in FIGS. 1 and 3.

The illustrated composite structure 40 includes an outer cover 46, a body side liner 48 which is connected to the outer cover 46 in a superposed relation, and an absorbent assembly 50 which is located between the outer cover 46 and the body side liner 48. The rectangular composite structure 40 has opposite linear end edges 52 that form portions of the front and back waist edges 38 and 39, and opposite linear, or curvilinear, side edges 54 that form portions of the side edges 36 of the absorbent chassis 32.

As shown in the swimpants 20 in FIGS. 1 and 2, the front and back regions 22 and 24 together define a three-dimensional pant configuration having a waist opening 58 and a pair of leg openings 60. The waist edges 38 and 39 of the absorbent chassis 32 are configured to encircle the waist of the wearer when worn and provide the waist opening 58 which defines a waist perimeter dimension. Portions of the transversely opposed side edges 36 (FIG. 3) in the crotch region 26 generally define the leg openings 60. The front region 22 includes the portion of the swimpant 20 which, when worn, is positioned on the front of the wearer while the back region 24 includes the portion of the swimpant 20 which, when worn, is positioned on the back of the wearer. The crotch region 26 of the swimpant 20 includes the portion of the swimpant 20 which, when worn, is positioned between the legs of the wearer and covers the lower torso of the wearer.

The absorbent chassis 32 is configured to contain and/or absorb any body exudates discharged from the wearer. For example, the absorbent chassis 32 can include a pair of elasticized containment flaps 62 (shown in FIGS. 2 and 3) which are configured to provide a barrier to the transverse flow of body exudates. More particularly, in terms of swimwear, the containment flaps 62 help prevent the escape of bowel movements from the swimpant 20. Furthermore, the containment flaps 62 provide pre-swim urine leakage protection when the absorbent assembly 50 can no longer acquire the incoming fluid at the rate at which it is being delivered.

The elasticized containment flaps 62 define an unattached edge 64 which assumes an upright, generally perpendicular configuration in at least the crotch region 26 of the swimpant 20 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

Absorbent swimwear is designed for leakage prevention prior to swimming. When a wearer wears absorbent swimwear into a pool or lake, the swimwear has a tendency to fill up with water. The swim water that enters the to swimwear mixes with the bodily excretions contained within the garment and may thereafter exit the garment, carrying with it various microorganisms from the bodily excretions. Solid waste is kept inside the swimpant 20 regardless of the release of the swim water, because the body side liner material 48 is constructed as in a normal absorbent garment, such as a diaper or training pant, to keep bowel movements contained therein. Nevertheless, microorganisms can still be carried by the water through the body side liner 48. Therefore, the swimpant 20 of this invention is equipped with biocidal and/or filtration agents to kill or immobilize the microorganisms in the water prior to or concurrent with the water's exit from the swimpant 20.

Figure 4:
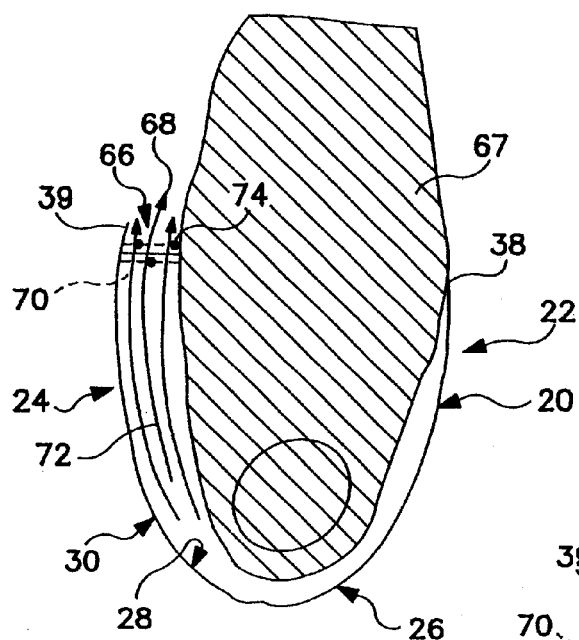
FIG. 4 is a cross-sectional view of the swimpant on a wearer, the swimpant having a porous waist dam and a binding agent.
Figure 5:
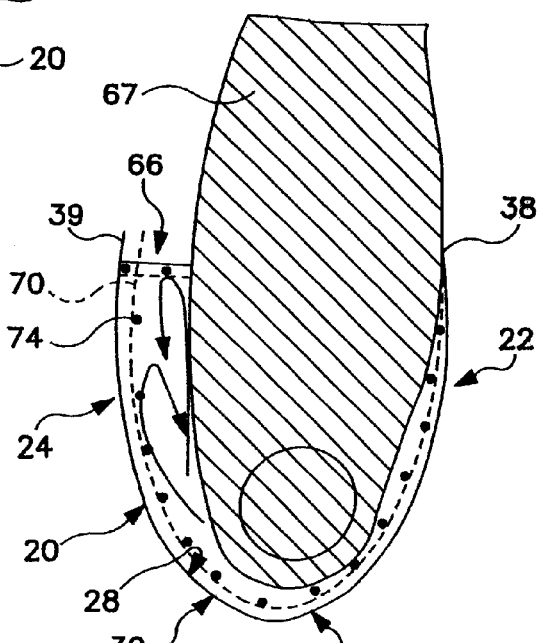
FIG. 5 is a cross-sectional view of the swimpant on a wearer, the swimpant having a non-porous waist dam and a binding agent.
Figure 6:
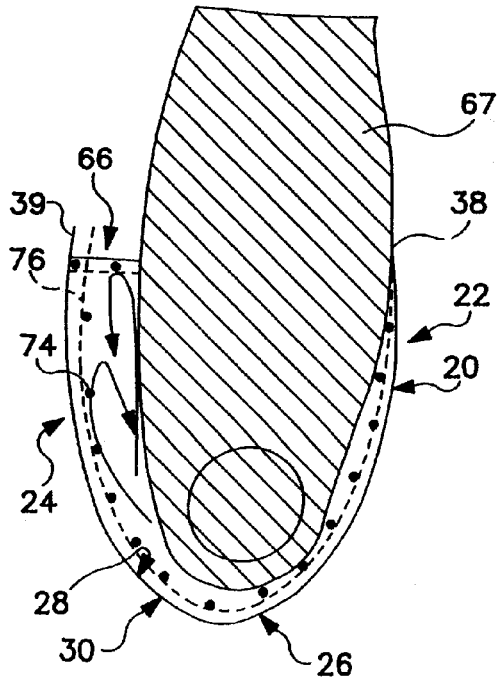
FIG. 6 is a cross-sectional view of the swimpant on a wearer, the swimpant having an antimicrobial agent.

FIGS. 4–6 illustrate cross-sections of a wearer 67 and a swimpant 20 disposed on the wearer 67. In one embodiment of the invention, a waist dam 66 is formed around the waist opening 58 of the swimpant 20. The waist dam 66 is an extension of the absorbent chassis 32 that bridges any gaps between the waistline of the wearer 67 and either or both of the waist edges 38 and 39 of the swimpant 20. U.S. Pat. No. 5,904,675 issued to Laux, et al., hereby incorporated by reference, describes waist dams in greater detail. Suitably, as shown in FIGS. 4–6, a waist dam 66 is located in the back region 24 of the swimpant 20, specifically between the wearer's waistline and the back waist edge 39, since swimpants normally fit more snugly around a wearer's front side than around the wearer's back side, and furthermore, because bowel movements are contained in the back region 24 of the swimpant 20.

The waist dam 66 can act as a filter; thereby allowing filtered water 68 to exit the swimpant 20 while retaining solid wastes and microorganisms within the swimpant 20. The waist dam 66 in this embodiment, shown in FIG. 4, is constructed from a porous nonwoven web which contains a filtration agent, or binding agent 70, therein. The binding agent 70 is capable of immobilizing microorganisms such as *E. coli* and other fecal associated bacteria, fungi and protozoans. The binding agent 70 is permanently attached within the waist dam 66. FIG. 4 shows swim water 72 intermingled with microorganisms inside the swimpant 20 and filtered swim water 68 that has passed through the waist dam 66. More particularly, binding sites 74 are illustrated as an example of showing that the unfiltered water 72 encounters the binding agent 70 at those binding sites 74 and is filtered upon exiting the swimpant 20.

In an alternative embodiment of the invention, the waist dam 66 is constructed of a non-porous material with the binding agent 70 fixed on the inner surface 28 of the swimpant 20, as shown in FIG. 5. More particularly, the binding agent 70 is attached to the inner surface of the body side liner 48 and the waist dam 66. In this embodiment, since water is not being filtered out of the swimpant 20 through the waist dam 66, water exchange between the inside and outside of the swimpant 20 is limited, thus providing sufficient time to immobilize the microorganisms. The swim water may leak into and out of the swimpant 20 through the waist opening 58 and the leg openings 60. The inclusion of containment flaps 62 reduces such leakage.

In further alternative embodiments of the invention, the binding agent 70 can be applied to the containment flaps 62, the outer cover 46, the absorbent assembly 50, and/or the body side liner 48 of the swimpant 20. In each of these embodiments, the binding agent 70 filters, or immobilizes, the swim water in the same manner as described with respect to the waist dam 66.

Suitable binding agents 70 that can be used to trap microorganisms include, but are not limited to, cationic compounds, biological cationic polymers, inorganic cationic species, and polymer matrices having modified charge. Examples of suitable cationic compounds include, but are not limited to, cationic polymers, charge modification of polymer matrices, inorganic cationic species, biological cationic polymers such as chitosan, debonder, quaternary ammonium, SILGARD®, octadecyldimethoxylsilylpropylammonium chloride, polyacrylamides (PAMS), diallydimethyl ammonium chloride (DADMAC), dicyandiamideformaldehyde, epichlorohydrin-amine (EPI type), cationic liposomes, modified starch, and many softeners. There are a number of materials that are used to obtain softness. Most quaternary ammonium compounds containing fatty acid chains and cationic silicones impart softness to some degree and affect the charge. Most bacteria are negatively charged, with zeta potentials ranging from 14.5 to 650 mV for gram positive bacteria, 6 to 160 mV for gram negative bacteria, and 20 mV for yeast. Cationic polymers with charge density ranges from about 0.1 to 1500 micro equivalents/gram are preferred to remove these microbes. All must be positively charged.

In yet another embodiment of this invention, the swimpant 20 includes a biocidal agent, or antimicrobial agent 76, capable of killing microorganisms such as *E. coli* and other fecal associated bacteria, fungi and protozoans. The antimicrobial agent 76 can be permanently fixed to internal substrates of the swimpant 20, such as the body side liner 48, as shown in FIG. 6, and the containment flaps 62, and can exhibit a broad spectrum of biocidal activity. Alternative substrates for the antimicrobial agent can include the absorbent assembly 50 or the waist dam 66.

Another alternative substrate for the antimicrobial agent 76 is the outer surface 30 of the outer cover 46. In this embodiment, the antimicrobial agent 76 is released to the aqueous environment. Once in the aqueous environment, the soluble biocide interacts with the microbes in a limited zone in and around the swimpant 20. This embodiment is effective for short-term use, since, over time, the biocidal capabilities are reduced by migration of the antimicrobial agent 76 out of and away from the swimpant 20, thus decreasing the effective concentration of the antimicrobial agent 76.

Suitable antimicrobial agents 76 that can be used to kill microorganisms include, but are not limited to, silver, quaternary ammonia compounds, stabilized oxidants, and antimicrobial peptides. More specifically, suitable examples include chloramine, hydantoin, halazone, trichloromelamineiodophors, halogenated phenols, bisphenols, peroxide, hydrogen peroxide, chlorhexidine, isothizolins, amphoteric surface-active agents (substituted glycines), silver acetate, silver citrate, silver lactate, silver sulfadiazine, colloidal silver, metals (copper, zinc, nickel). There are many more specific examples that would be known to one skilled in the art.

Both the binding agent 70 and the antimicrobial agent 76 can be used simultaneously within the swimpant 20. The binding agent 70 and/or the antimicrobial agent 76 can be attached to any one or more of the components of the swimpant 20, including the waist dam 66, the containment flaps 62, the outer cover 46, the body side liner 48, and the absorbent assembly 50.

The absorbent assembly 50, positioned between the outer cover 46 and the body side liner 48, can be any structure which is generally compressible, conformable, non-irritating to the child's skin, and capable of absorbing and retaining liquids and certain body wastes. The absorbent assembly 50 can be manufactured in a wide variety of sizes and shapes, and from a wide variety of liquid absorbent materials commonly used in the art. For example, the absorbent assembly 50 can suitably include a matrix of hydrophilic fibers, such as a web of cellulosic fluff, mixed with particles of a high-absorbency material commonly known as superabsorbent material. In a particular embodiment, the absorbent assembly 50 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 50 to better contain and absorb body exudates. The concentration of the superabsorbent particles can also vary through the thickness of the absorbent assembly 50. Alternatively, the absorbent assembly 50 can include a laminate of fibrous webs and superabsorbent material or other suitable means of maintaining a superabsorbent material in a localized area. Another type of absorbent material suitable for the absorbent assembly 50 is co-form, which is a blend of staple length and melt-blown fibers. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Superabsorbent materials may be added to the co-form to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 50 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 50 in an amount of from about 0 to about 90 weight percent based on total weight of the absorbent assembly 50. The absorbent assembly 50 suitably has a density within the range of about 0.10 to about 0.35 grams per cubic centimeter. The absorbent assembly 50 may or may not be wrapped or encompassed by a suitable tissue wrap that maintains the integrity and/or shape of the absorbent assembly 50.

The absorbent chassis 32 can also incorporate other materials that are designed primarily to receive, temporarily store, and/or transport liquid along the mutually facing surface with the absorbent assembly 50, thereby maximizing the absorbent capacity of the absorbent assembly 50. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

The outer cover 46 desirably includes a material that is substantially liquid impermeable, and can be elastic, stretchable or nonstretchable. The outer cover 46 can be a single layer of liquid impermeable material, but desirably includes a multi-layered laminate structure in which at least one of the layers is liquid impermeable. For instance, the outer cover 46 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable body side liner 48 is made. While it is not a necessity for the outer layer to be liquid permeable, it is desired that it provides a relatively cloth-like texture to the wearer.

The inner layer of the outer cover 46 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 46 when a single layer, prevents waste material from wetting articles, such as car seats and clothing, as well as the wearer and care giver. A suitable liquid impermeable film for use as a liquid impermeable inner layer, or a single layer liquid impermeable outer cover 46, is a 0.2 millimeter polyethylene film commercially available from Huntsman Packaging of Newport News, Va., U.S.A. If the outer cover 46 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable body side liner 48 is illustrated as overlying the outer cover 46 and absorbent assembly 50 (FIG. 3), and may but need not have the same dimensions as the outer cover 46. The body side liner 48 is desirably compliant, soft feeling, and non-irritating to the child's skin. Further, the body side liner 48 can be less hydrophilic than the absorbent assembly 50, to present a relatively dry surface to the wearer and permit liquid to readily penetrate through its thickness.

The body side liner 48 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 48. For example, the body side liner 48 can be composed of a meltblown or spunbonded web of polyolefin fibers. The body side liner 48 can also be a bonded-carded web composed of natural and/or synthetic fibers. The body side liner 48 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire body side liner 48 or can be selectively applied to particular sections of the body side liner, such as the medial section along the longitudinal centerline.

A suitable liquid permeable body side liner 48 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 46 and body side liner 48 can include elastomeric materials, it can be desirable in some embodiments for the composite structure to be generally inelastic, where the outer cover 46, the body side liner 48 and the absorbent assembly 50 include materials that are generally not elastomeric.

The containment flaps 62 may be made of those materials of which the outer cover 46 and/or the body side liner 48 is made.

As noted previously, the illustrated swimpant 20 can have front and back side panels 42 and 44 disposed on each side of the absorbent chassis 32 (FIGS. 1 and 3). These transversely opposed front side panels 42 and transversely opposed back side panels 44 can be permanently bonded to the composite structure 40 of the absorbent chassis 32 and can be permanently bonded to one another along corresponding sides. Alternatively, the front and back side panels 42, 44 can be releasably attached to one another by a fastening system 78. The side panels 42 and 44 may be attached to the composite structure 40 and/or to one another using attachment means known to those skilled in the art such as adhesive, thermal or ultrasonic bonding. The side panels 42 and 44 can also be formed as a portion of a component of the composite structure 40, such as the outer cover 46 or the body side liner 48.

Suitable elastic materials, as well as one described process of incorporating elastic side panels into an absorbent garment, are described in the following U.S. Pat. No.: 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretchthermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 46 or body side liner 48, or stretchable but inelastic materials.

To further enhance containment and/or absorption of body exudates, the swimpant 20 can include waist elastic members 82 and/or leg elastic members 84, as are known to those skilled in the art (FIGS. 1–3). The waist elastic members 82 can be operatively joined to the outer cover 46 and/or to the body side liner 48, and can extend over part or all of the waist edges 38, 39. The leg elastic members 84 are desirably operatively joined to the outer cover 46 and/or to the body side liner 48 longitudinally along the opposite side edges 36 and positioned in the crotch region 26 of the swimpant 20.

The waist elastic members 82 and the leg elastic members 84 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 82 and/or the leg elastic members 84 include a plurality of dry-spun coalesced multifilament spandex elastomeric threads sold under the trade name LYCRA® and available from E.I. du Pont de Nemours and Company, Wilmington, Del., U.S.A. In another particular embodiment, for example, the waist elastic members 82 and/or the leg elastic members 84 include Findley HX 2695-01 adhesive laminated to two facings of 0.6 osy (ounces per square yard) bicomponent polypropylene/polyethylene spunbond. Alternatively, six strands of 310 decitex LYCRA® may be also laminated at 250% elongation between the spunbond facings in addition to the Findley adhesive.

As described herein, the various components of the swimpant 20 can be integrally assembled together employing various types of suitable attachment means, such as adhesive, sonic and thermal bonds or combinations thereof. The resulting product is an absorbent swimwear garment 20 that provides uncompromised urine and bowel movement containment before swimming, and includes a microbial management system for killing or immobilizing microorganisms in swim water, such as pool or lake water, inside the garment during swimming.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A swimwear garment comprising:
   a chassis defining a waist opening and first and second leg openings; and a binding agent attached to the garment and capable of filtering out microorganisms; wherein the binding agent comprises a substance selected from the group consisting of cationic polymers, biological cationic polymers, inorganic cationic species, and polymer matrices having modified charge.

2. The swimwear garment of claim 1, further comprising a waist dam around the waist opening of the chassis.

3. The swimwear garment of claim 2, wherein the binding agent is attached to the waist dam.

4. The swimwear garment of claim 2, wherein the waist dam comprises a porous, nonwoven web, and the binding agent is contained within the nonwoven web.

5. The swimwear garment of claim 2, wherein the waist dam comprises a non-porous material, and the binding agent is attached to a surface of the non-porous material.

6. The swimwear garment of claim 1, wherein the chassis further comprises a body side liner, an outer cover, and an absorbent assembly between the body side liner and the outer cover.

7. The swimwear garment of claim 6, wherein the binding agent is attached to the body side liner.

8. The swimwear garment of claim 6, wherein the binding agent is attached to the outer cover.

9. The swimwear garment of claim 6, wherein the binding agent is attached to the absorbent assembly.

10. The swimwear garment of claim 1, further comprising a pair of containment flaps around the leg openings of the chassis.

11. The swimwear garment of claim 10 wherein the binding agent is attached to the containment flaps.

12. The swimwear garment of claim 1, wherein the binding agent comprises chitosan.

13. A swimwear garment comprising:
    a chassis defining a waist opening and first and second leg openings, the chassis including a body side liner, an outer cover, and an absorbent assembly between the body side liner and the outer cover;
    a binding agent attached to the garment, wherein the binding agent is capable of filtering out microorganisms and comprises a substance selected from the group consisting of cationic polymers, biological cationic polymers, inorganic cationic species, and polymer matrices having modified charge; and
    an antimicrobial agent attached to the garment.

14. The swimwear garment of claim 13, wherein the binding agent is attached to the body side liner.

15. The swimwear garment of claim 13, wherein the antimicrobial agent is attached to the body side liner.

16. The swimwear garment of claim 13, wherein the binding agent is attached to the outer cover.

17. The swimwear garment of claim 13, wherein the antimicrobial agent is attached to the outer cover.

18. The swimwear garment of claim 13, wherein the binding agent is attached to the absorbent assembly.

19. The swimwear garment of claim 13, wherein the antimicrobial agent is attached to the absorbent assembly.

20. The swimwear garment of claim 13, further comprising a waist dam around the waist opening of the chassis.

21. The swimwear garment of claim 20, wherein the binding agent is attached to the waist dam.

22. The swimwear garment of claim 20, wherein the antimicrobial agent is attached to the waist dam.

23. The swimwear garment of claim 13, further comprising a pair of containment flaps around the leg openings of the chassis.

24. The swimwear garment of claim 23, wherein the binding agent is attached to the containment flaps.

25. The swimwear garment of claim 23, wherein the antimicrobial agent is attached to the containment flaps.

26. The swimwear garment of claim 13, wherein the antimicrobial agent comprises a substance selected from the group consisting of silver, quaternary ammonia compounds, stabilized oxidants, and antimicrobial peptides.

* * * * *

UNITED STATES PATENT AND TRADEMARK OFFICE
CERTIFICATE OF CORRECTION

PATENT NO.   : 6,797,856 B1
DATED        : September 28, 2004
INVENTOR(S)  : Kolb et al.

It is certified that error appears in the above-identified patent and that said Letters Patent is hereby corrected as shown below:

Substitute the drawings with the attached formal drawings.

Signed and Sealed this

First Day of November, 2005

JON W. DUDAS
*Director of the United States Patent and Trademark Office*